United States Patent [19]

Alexander et al.

[11] Patent Number: 4,589,958

[45] Date of Patent: * May 20, 1986

[54] METHOD OF POTENTIOMETRIC DETECTION OF COPPER-COMPLEXING AGENTS

[75] Inventors: Peter W. Alexander, Maroubra; Paul R. Haddad, Eastwood, both of Australia

[73] Assignee: Unisearch Limited, Kensington, Australia

[*] Notice: The portion of the term of this patent subsequent to May 21, 2002 has been disclaimed.

[21] Appl. No.: 697,935

[22] Filed: Feb. 4, 1985

Related U.S. Application Data

[63] Continuation-in-part of Ser. No. 484,703, Apr. 13, 1983, Pat. No. 4,518,463, which is a continuation of Ser. No. 249,373, Mar. 31, 1981, abandoned.

[51] Int. Cl.$^4$ ............................................. G01N 27/46
[52] U.S. Cl. .................................... 204/1 T; 204/292; 204/400; 204/409
[58] Field of Search .............. 204/1 T, 1 N, 1 K, 292, 204/400, 409

[56] References Cited

U.S. PATENT DOCUMENTS

| | | | |
|---|---|---|---|
| 3,043,764 | 7/1962 | Harvey | 204/402 |
| 3,051,631 | 8/1962 | Harbin et al. | 204/1 T |
| 3,367,849 | 2/1968 | Blazdel et al. | 204/403 |
| 3,556,950 | 1/1971 | Dahms | 204/412 |
| 4,058,446 | 11/1977 | Zirino et al. | 204/434 |
| 4,299,669 | 11/1981 | Obana et al. | 204/1 N |

FOREIGN PATENT DOCUMENTS 0687385  9/1979  U.S.S.R. ............................. 204/1 K

OTHER PUBLICATIONS

Keenan et al., J. Electrochemical Soc., 1976, vol. 123, pp. 179–182.
Alexander et al., Reprint from *Analytical Chemistry*, vol. 53, No. 11, Sep. 1981, pp. 1590–1594.
Lange, N. A., ed., "Handbook of Chemistry", Tenth Edition, McGraw-Hill Book Co., Inc., New York 1961; 952.
Toribara, T. Y.; Koval, L., *Talanta*, 1970, 17, 1003–1006.
Nikolelis, D. P.; Papastathopoulos, D. S.; Hadjiioannou, T. F., *Anal. Chim. Acta*, 1978, 98, 227–232.
Heijne, G. J. M.; van der Linden, W. E., *Anal. Chim. Acta*, 1978, 96, 13–22.
Ferrel, E.; Ridgion, J. M.; Riley, H. L., *J. Chem. Soc.*, 1934, 1440–1447.
Williams, D. R., *J. Chem. Soc.*, (Dalton), 1972, 790–797.
Loscombe, G. R.; Cox, G. B., Dalrick, J. A. W., *J. Chromatog.*, 1978, 166, 403–410.
Vogel, A. I., "A Textbook of Quantitative Inorganic Analysis", Third Edition, Longmans, London, 1961; 35.
Sekerka, I.; Lechner, J. F., *Anal. Bett.*, 1978, A11(5), 415–427.
Westall, J. C.; Morel, F. M. M.; Hume, D. N., *Anal Chem.*, 1979, 51, 1792–1798.
Laitinen, H. A.; Harris, W. E., "Chemical Analysis", 2nd ed.; McGraw-Hill, New York, 1975; pp. 227–233.
Midgley, D.; Torrance, K., "Potentiometric Water Analysis", J. Wiley and Sons, New York, 1978; pp. 17, 126–127.
Doran, M. A.; Chaberek, S.; Martell, A. E., *J. Amer. Chem. Soc.*, 1964, 86, 2129–2135.
El–Taraz, M. F.; Pungor, E., *Anal. Chim. Acta*, 1976, 82, 285–292.
Olson, V. K.; Carr, J. D.; Hargens, R. D.; Ken Force, *Anal. Chem.*, 1976, 48, 1228–1231.
Van der Linden, W. E.; Oostervink, R., *Anal. Chim. Acta*, 1978, 101, 419–422.
Van der Meer, J. M.; den Boef, G. and Van der Linden, W. E., *Anal. Chim. Acta*, 1976, 85, 309–316.
Ross, J. W.; Frant, M. S., *Anal. Chem.*, 1969, 41, 1900–1902.
Hassan, S. S. M.; Zaki, M. T. M., *Mikrochim. Acta*, 1979, I, 137–144.

*Primary Examiner*—T. Tung
*Attorney, Agent, or Firm*—Murray and Whisenhunt

[57] ABSTRACT

A method of directly detecting amino acids, other organic and inorganic copper-complexing agents, and indirectly detecting non copper-complexing species comprising use of a potentiometric flow-through electrode detector suitable for use in high performance liquid chromatography and autoanalyzers. Said detector comprises a copper metal indicator electrode and a suitable reference electrode within a miniature flow through cell and which detector has the property that it provides a voltage response to the particular molecule to be detected thereby.

5 Claims, 11 Drawing Figures

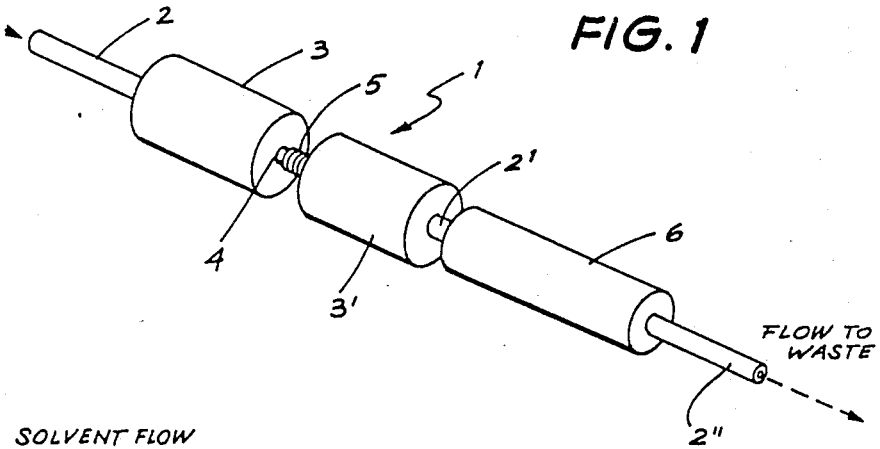
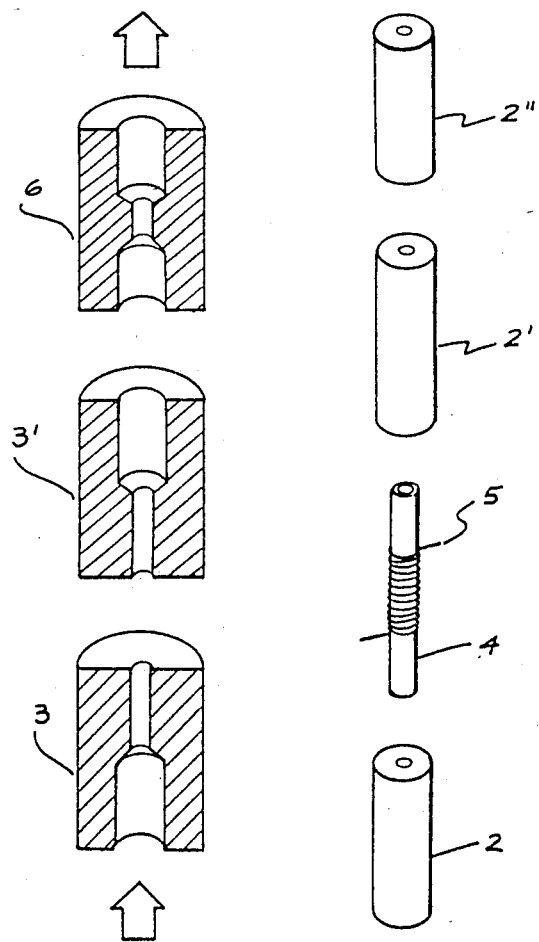

METHOD OF POTENTIOMETRIC DETECTION OF COPPER-COMPLEXING AGENTS

The present invention relates to detectors and more particularly to detectors for use in detecting the presence of chemicals.

The present application is a continuation-in part of Application Ser. No. 484,703 filed April 13, 1983 assigned to the assignee of the present application. now U.S. Pat. No. 4,518,463, which is a continuation of application Ser. No. 249,373 filed Mar. 31, 1981, now abandoned, all.

Conventional methods of detection and electrode detectors as are used in, say, High Performance Liquid Chromatography (HPLC) or Autoanalyzers are based upon voltammetric methods whereby a current resulting from an applied voltage is measured. Such electrode detectors are complex and subject to interference problems in use. Even more complex and expensive is the use of spectroscopic detectors which are most often supplied in association with present HPLC and autoanalyzers.

The present invention proposes a method of detecting amino acids and other organic copper-complexing agents employing a potentiometric electrode detector comprising a copper metal electrode located within a flow through cell adapted to be flow-coupled to, say, the effluent from a liquid chromatograph column or continuous flow analyzer, said electrode and a reference electrode being adapted for electrical connection to a voltage controller and recording means whereby changes in voltage at the copper metal electrode due to copper-complexing are recorded. The flow through cell has a volume of 0.2 to 2 $\mu$ with the reference electrode within the cell.

In one embodiment, the method of the present invention employs a potentiometric electrode detector comprising a chemically inert flow through cell housing a copper wire electrode. A branch of the cell houses a reference electrode. Control of the flow-through cell volume by employing a copper wire electrode within an inert cell has been found to be the most efficient means. In experiments employing this form of potentiometric detector metal ions have been detectable. The reference electrode in that case has been formed from silver-silver chloride placed in agar-agar gel containing potassium chloride.

In a further embodiment of electrode detector, the copper metal electrode is in the form of a metallic copper tube forming at least part of the flow through cell and the reference electrode is of platinum. With the method of the present invention the following classes of chemicals have been found to be detectable.

| | |
| --- | --- |
| Biological Species: | Amino acids, proteins, enzymes and enzyme substrates. |
| Pharmaceuticals: | Penicillins, sulphonamides, vitamins. |
| Complexing Agents: | EDTA, ethylenediamine, ammonia. |
| Oxidising Agents: | Hydrogen peroxide, nitric acid. |
| Metals: | All metals capable of reacting with EDTA can be indirectly detected. |

The copper metal electrode has advantages which include it only provides a response to copper-binding molecules and strong redox reagents such that it suffers from fewer background interference problems than present spectroscopic or voltammetric detectors when used for the analysis of complex samples such as blood and urine, etc. Where the electrode detector is miniaturised say having a volume of 0.4 $\mu$l, sharp HPLC peaks can be obtained.

The present invention will now be described by way of example with reference to a copper-platinum potentiometric electrode used as a detector for the determination of amino acids by HPLC ano a copper-silver/silver chloride potentiometric electrooe used as a detector for the determination of metal ions.

In the drawings:

FIG. 1 is a perspective view of a first electrode detector in accordance with the invention;

FIG. 2 is an exploded view of the electrode detector of FIG. 1;

Figure 10:
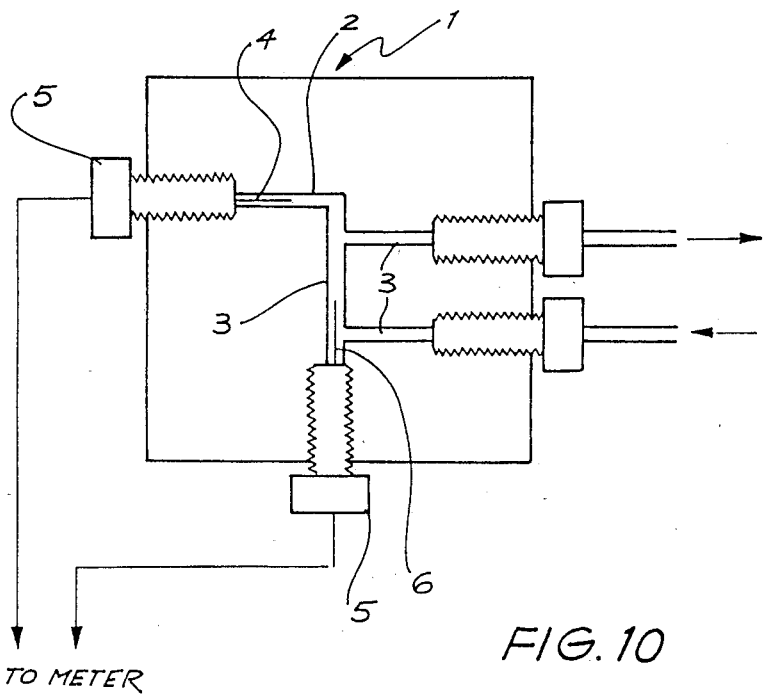
Figure 11:
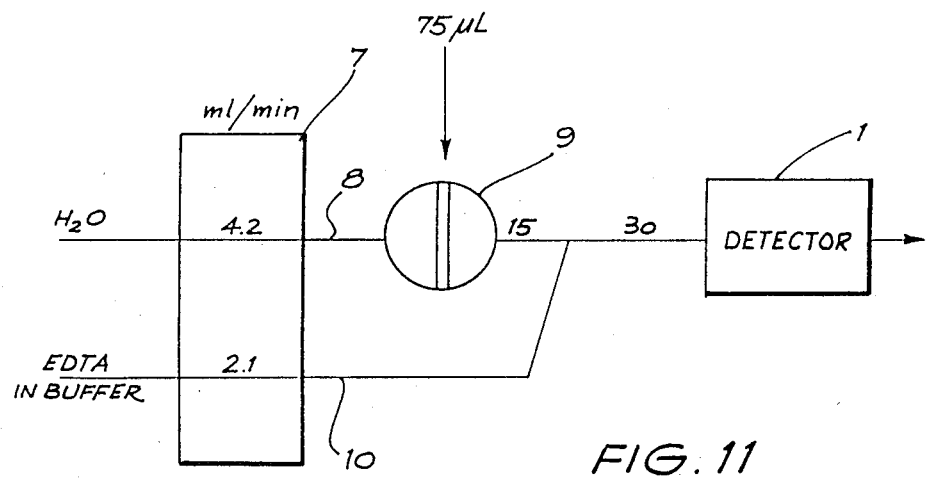

FIGS. 6 to 9 relate to plots derived from the example and are described hereinafter;

FIG. 10 is a schematic diagram of a second form of detector for carrying out the method of the present invention; and FIG. 11 is a schematic representation of the flow system for metal ion determination using the dector of FIG. 10.

Referring to FIGS. 1 and 2 there is shown an electrode detector 1 comprised of tubular flow-through components. The detector 1 has a Teflon inlet part comprising a Teflon tubing part 2 fitted into a Teflon mounting part 3. Fitted into part 3 is a platinum reference electrode tube 4 wrapped with a wire contact 5. The other end of platinum electrode 4 is mounted in a further Teflon mounting part 3' which is coupled via Teflon tube 2' to a flow-through copper electrode 6. The exit from copper electrode 6 is through a further Teflon tube 2". In use flow enters the detector from a flow absorbance detector via tube 2 and after passing through detector 1 exits via tube 2".

The following description concerns an example of the use of the detector of this embodiment from which its advantages will be readily appreciated.

EXAMPLE

In this example, we describe the use of a copper tubular electrode as a sensitive and selective detector in the analysis of amino acids by HPLC. A recent paper submitted by P. W. Alexander ano C. Maitra to Anal. Chem. entitled "Continuous-flow potentiometric monitoring of $\alpha$ - amino acids with copper wire and tubular electrodes" reports the use of copper wire and copper tubular electrodes as sensitive universal detectors in continuous flow systems, where they were found to be superior to the copper selective membrane electrode for direct quantitation of amino acids. This system is shown to be useful as a detector for amino acids without post-column reaction of the eluted amino acids with $Cu^{2+}$.

Instrumentation

Figure 3:
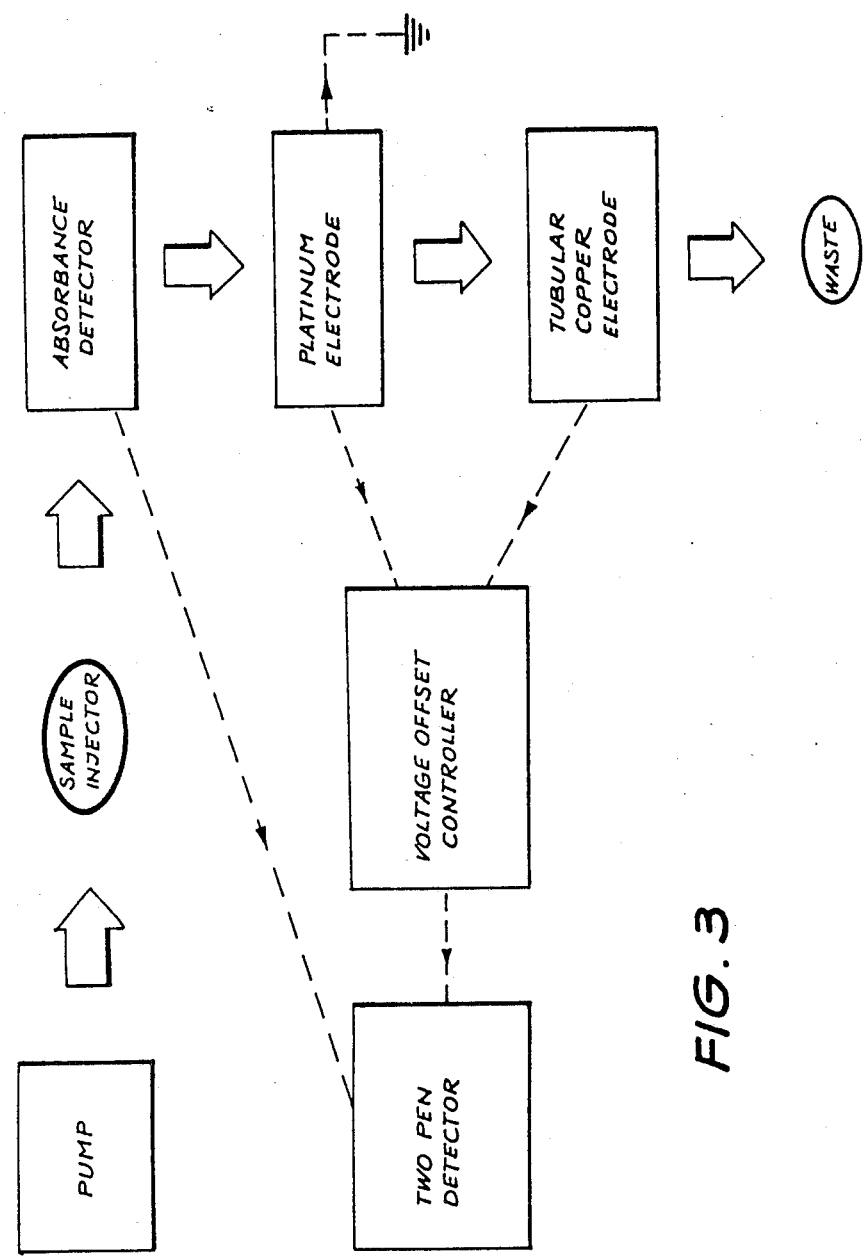
FIG. 3 is a schematic diagram of a flow system used in an example of operation of the detector of FIGS. 1 and 2 connected in series with a UV absorbance detector.

A schematic diagram of the flow system used is shown in FIG. 3. In this system, a Waters model 6000 solvent pump, a Waters Model U6K injector, a Waters Model 450 variable wavelength detector and the electrode detector were linked serially in flow to each other. The electrode detector (FIGS. 1 and 2) consisted of two tubular electrodes, one of copper and one of platinum, both of which were connected to an Activon voltage offset controller ($\pm 1.5$ V) and the platinum electrode was grounded. The outputs from the UV detector and the voltage controller were linked to a two pen Omniscribe Model B 5271 recorder, which had a 10 mV input.

The components of the electrode detector system were as follows. The internal flow copper tubular electrode was constructed from 0.5 cm diam. copper rod, 2 cm in length. This rod was precisely drilled to give an internal diameter of 0.75 mm for the flow path, the length of which was varied over the range 0.5–5.0 mm, however 1 mm was most frequently used. The platinum electrode was a 1 cm length of platinum tubing (0.75 mm ID) sandwiched between two pieces of Teflon tubing which served both to mechanically support the platinum electrode and to provide a means of attaching the flow tubing used to interconnect the various components of the system.

Reagents and Stock Solutions

Amino acids were obtained from various sources: glycine from BDH Biochemicals; valine from Koch Light and Co.; l-isoleucine from BDH Ltd; Methionine from NBC and phenylalanine from Merck. The amino acids were used without further purification and standard solutions were prepared immediately prior to use by dissolving weighed amounts in pH 6.7 buffer. This buffer solution was prepared from AR sodium hyoroxide and potassium dihydrogen phosphate (BDH Chemicals).

Volucon standard buffers were used to calibrate the pH meter.

The mobile phase used for the HPLC separation of amino acids was prepared by mixing 50 ml of 1M $NaH_2$-$PO_4$, 19.2 ml of 1M NaOH and 10.0 ml of 40% w/v formaldehyde in a 1l volumetric flask. The solution was then diluted to the mark to give a final pH of $6.7\pm 0.1$. All water used for the chromatographic procedure was distilled and passed through a Millipore Q Water Purification System before use and methanol was triply distilled using all glass apparatus.

The urine control sample was obtained from Travenol Laboratories (USA) and was freshly reconstituted prior to use. The pharmaceutical intravenous amino acid solution was also obtained from Travenol, under the trade name "Synthamin 17" and contained 9 essential and 6 non-essential amino acids in concentrations ranging from 400 mg - 21 g per liter. This solution was diluted by a factor of 25 for chromatographic runs. Both urine and the intravenous solution were filtered through a 2.5 $\mu$m Millipore filter before injection into the chromatograph.

Chromatographic Procedure

Separation by HPLC was accomplished using a $\mu$-Bondapak C18 column (30 cm$\times$3.9 mm I.D., Waters Associates) maintained 25° C. The column was standardised using the manufacturer's recommended procedure and gave counts in the region of 4000 theoretical plates. The mobile phase flow rate was set at 1 ml/min (unless otherwise stated), producing a back pressure of 1000 psi. The absorbance detector was operated at 200 nm using a sensitivity setting of 0.1 AUFS.

In this study, all eluted compounds were detected both by the UV detector and the copper electrode and the peaks displayed on the two pen recorder using a chart speed of 1 cm/min. Each data point shown in this paper represents the mean of triplicate injections.

To prevent a decrease in sensitivity of the copper electrode due to poisoning, the electrode surface was periodically regenerated by rapid flushing with 5 ml of 8M $HNO_3$ followed by 20 ml of distilled water and 20 ml of methanol. When the electrode was stored in the flow system, a solvent consisting of 50:50 v/v methanol/water adjusted to pH~5 was used to prevent deterioration of the electrode.

Results and Discussion

Mobile Phase

The effect of pH on the response of the copper tubular electodce (CTE) was discussed in the previously referenced paper by Alexander and Maitra wherein it was shown that sensitivity for amino acid detection was greatest at high pH values. In this study the optimum pH for the mobile phase was determined to be 6.7 which represented a compromise between attainment of maximum sensitivity and the prevention of electrode poisoning.

Figure 4:
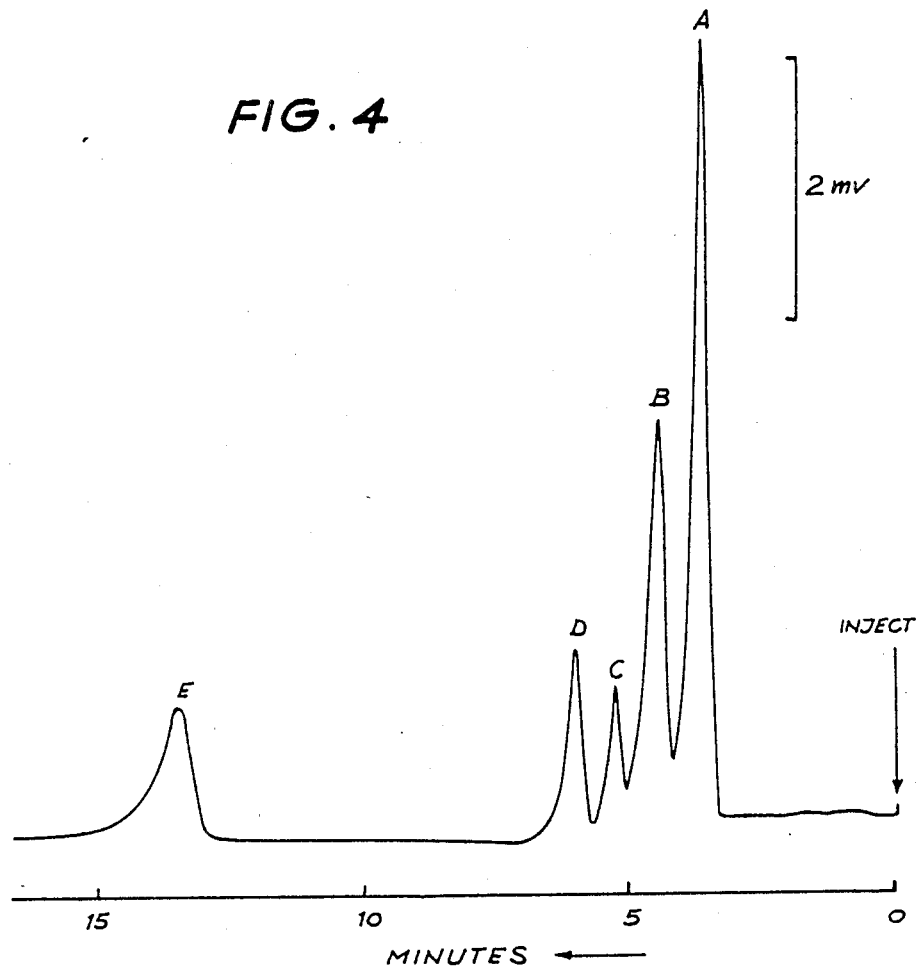
FIG. 4 shows a typical chromatogram of a separation of five amino acids using the system of FIG. 3.

FIG. 4 shows a typical chromatogram of a separation of five amino acids using the CTE as the detector system.

A slightly acidic mobile phase was necessary to discourage the formation of insoluble cupric hydroxides, carbonates and phosphates on the inner surface of the CTE. The ready formation of such compounds in alkaline media would result in potential drift leading to error in the measured concentration.

The purpose of formaldehyde in the mobile phase was to repress negative deviation of the baseline which occurred most prominently prior to the peaks due to sulphur containing amino acids such as methionine and cysteine. The exact mechanism whereby formaldenyde can eliminate such negative baseline deviations is not clear, but its reducing properties may assist in improving the rate of exchange of the amino acids on the electrode surface.

Reference electrode

The platinum tubular electrode shown in FIG. 1 was used for two purposes. Firstly, it acted as an auxiliary electrooe to reduce electrical noise and secondly, it served as a reference electrode to the CTE. Since it was electrically grounded, the reference used was the earth potential. This confirguration was adopted only after considerable experimentation with conventional reference electrodes, however, we found that the electrically grounded platinum electrode gave greatest sensitivity and least baseline noise.

Electrode flow path

Using glycine as a representative amino acid, the electrode response was studied as a function of the length of the electrode flow path for solutions of three different concentrations of glycine (5.8 $\mu$g,/$\mu$l, 11.5 $\mu$g/$\mu$l and 17.4 $\mu$g/$\mu$l) In all cases, the electrode signal reached a maximum for a flow path of 1.0 mm.

Poor response for very short flow paths is considered to be due to the relatively short residence times of the amino acid ligands in the electrode, whereas reduced response in tne longer path length electrodes is due to sample dispersion effects. The optimum flow path length of 1 mm was adopted for all further work.

Flow rate

The effect of flow rate on response time and sensitivity was studied by removing the HPLC column, replacing it with a suitable connector and then injecting glycine (3.4 µg/µl) at various flow rates. Values of $t_{max}$, the time required to reach the maximum of the chromatographic peak were measured for each flow rate and the results are shown in Table I.

TABLE I

Response characteristics of the CTE and absorbance detectors at various flow rates.
$t_{max}$ is the time taken to reach the peak maximum

| Flow rate | Peak height (mm) | | $t_{max}$ (sec) | |
|---|---|---|---|---|
| (ml/min) | UV detector | CTE | UV detector | CTE |
| 0.5 | 122 | 87 | 24.2 | 27.0 |
| 1.0 | 90 | 88 | 13.3 | 15.8 |
| 2.0 | 57 | 74 | 6.9 | 8.5 |
| 3.0 | 42 | 63 | 4.6 | 5.5 |
| 4.0 | 37 | 58 | 3.5 | 4.0 |

In agreement with earlier findings, the CTE response improved with increasing flow rate, however this was accompanied by a decrease in sensitivity due to the decreased residence time of the amino acid in the electrode. The response time of the CTE compared favourably with that of the absorbance detector while the sensitivity of the CTE as measured by peak height, was less dependent on flow rate than was the sensitivity of the absorbance detector. It is clear that the optimum flow rate selected would represent a compromise between response and sensitivity; in this study we used a flow rate of 1.0 ml/min.

Figure 6:
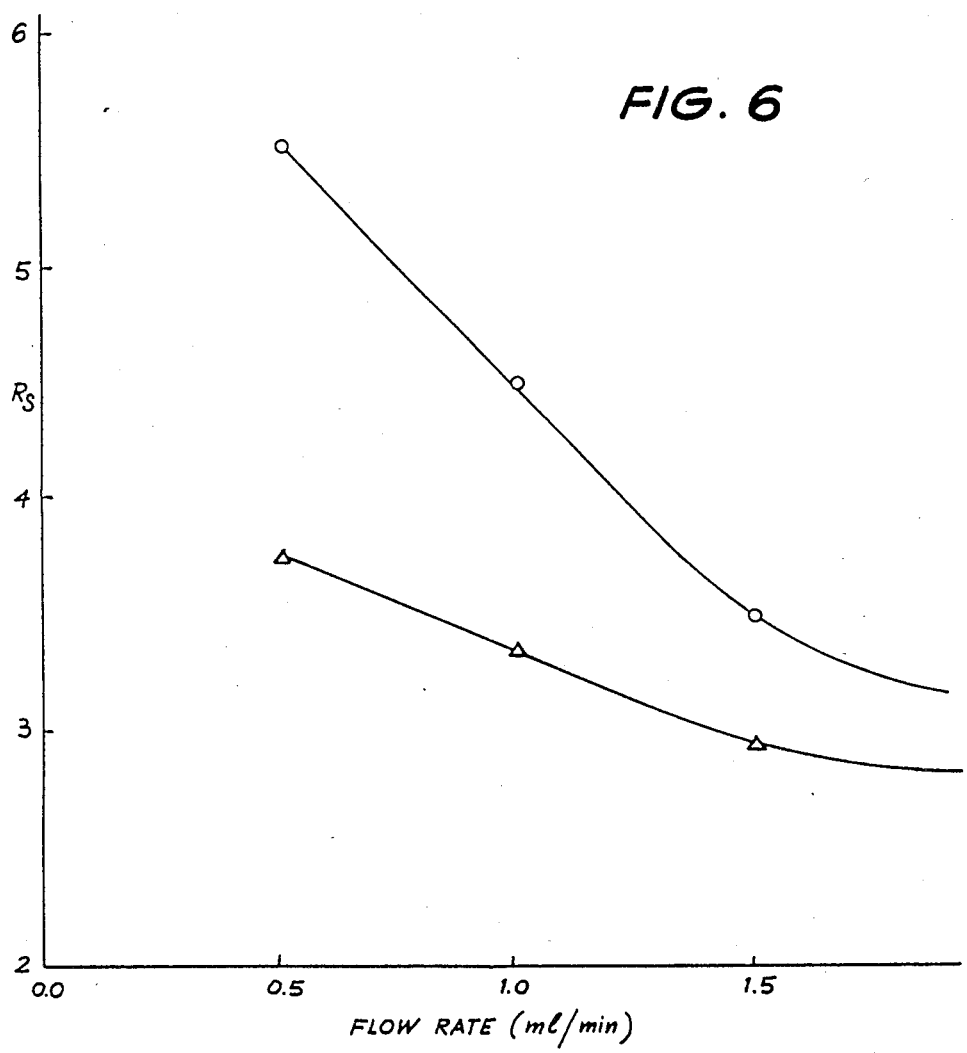

The relationship between flow rate and resolution was also examined to provide additional information on the response of tne CTE. Injections of 1 µl of a solution containing 11.5 and 8.8 µg/µl of glycine and isoleucine, respectively, were made at various values of solvent flow rate and the resolution ($R_s$) of the two resulting peaks was calculated using the conventional formula. For values of $R_s<0.8$, peaks are considered to be only partially resolved, whereas $R_s>2$ indicates resolution with at least two peak basewidths between peak maxima. The results obtained are shown in FIG. 6 using the electrode detector (66) and the UV absorbance detector (O).

A decrease in resolution with increasing solvent flow rate was observed for both the absorbance detector and the CTE, however it was observed that resolution achieved with the absorbance detector declined much more rapidly than for the CTE. It is noteworthy however that at all flow rates tested, the UV detector gave slightly superior resolution.

Calibration

Figure 5:
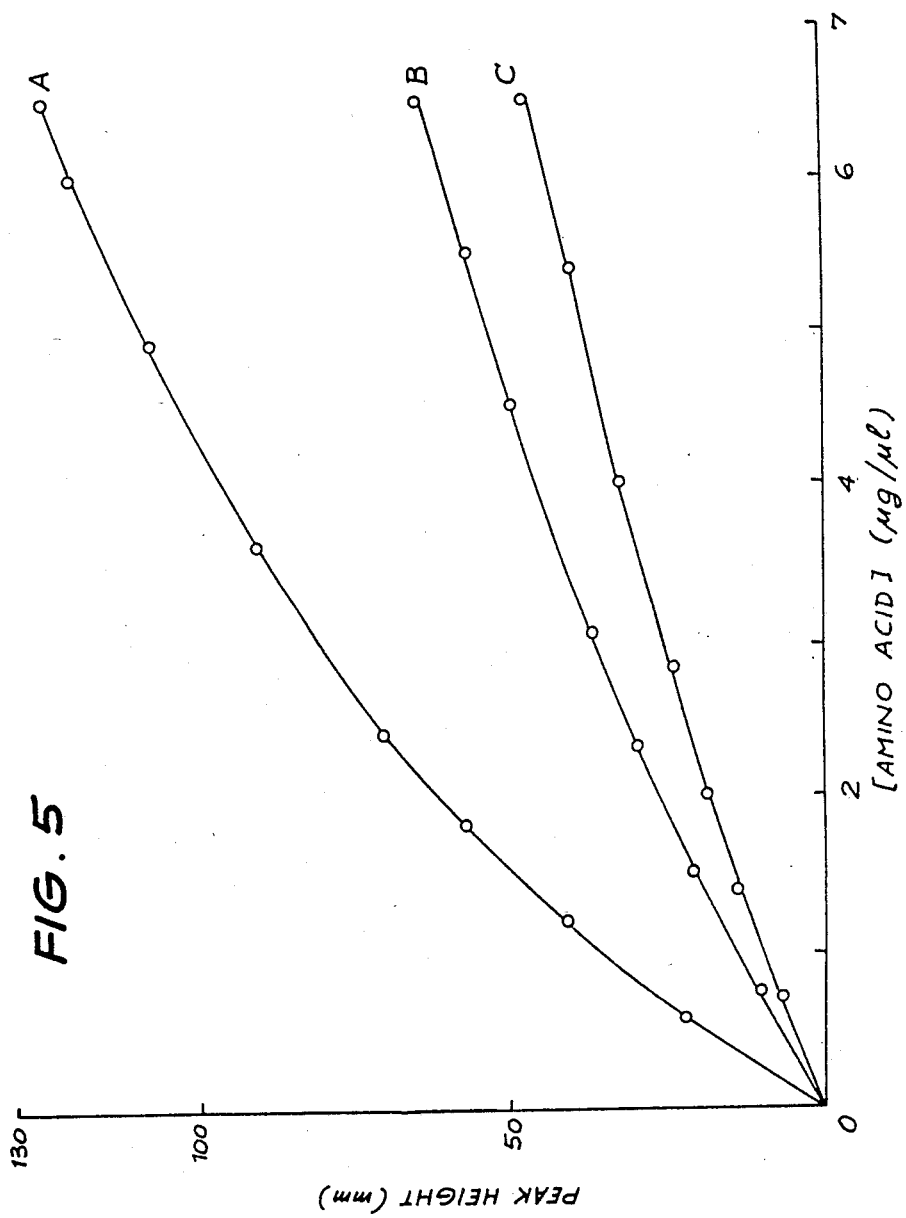
FIG. 5 shows calibration plots for the electrode detector system as used in the example.

Calibration curves for glycine, valine and isoleucine were prepared using both tne absorbance detector and the CTE. Linear plots were obtained with the UV detector for the three amino acids in the concentration range 0–25 µg/µl. The calibration plots obtained for the CTE were non-linear and are shown in FIG. 5; the electrode response follows the elution order glycine (A), valine (B), isoleucine (C). The shapes of the CTE calibration plots are similar to those obtained by Loscombe et al. J. Chromatogr. 166 (1978) 403 in their work based on a copper selective membrane electrode.

The precision of the electrode response was estimated by ten replicate injections of a solution containing glycine and isoleucine at concentrations of 1.74 µg/µl and 1.30 µg/µl respectively. Coefficients of variation of 1.4% for glycine and 2.5% for isoleucine were obtained and these results compared favourably witn the absorbance detector which gave coefficients of variation of 4.0% and 3.6%, respectively, for the same 10 injections.

Using a definition of detection limit as three times the baseline noise, tne calculated detection limits for glycine, valine and isoleucine were 75, 200 and 300 ng, respectively, in a 1 µl injection.

We are currently developing a combined recorder offset and signal amplification system which will permit detection of smaller amounts of amino acids than stated above. Initial studies have shown tnat a ten fold increase in sensitivity over the above values can be easily attained.

Applications

Figure 7:
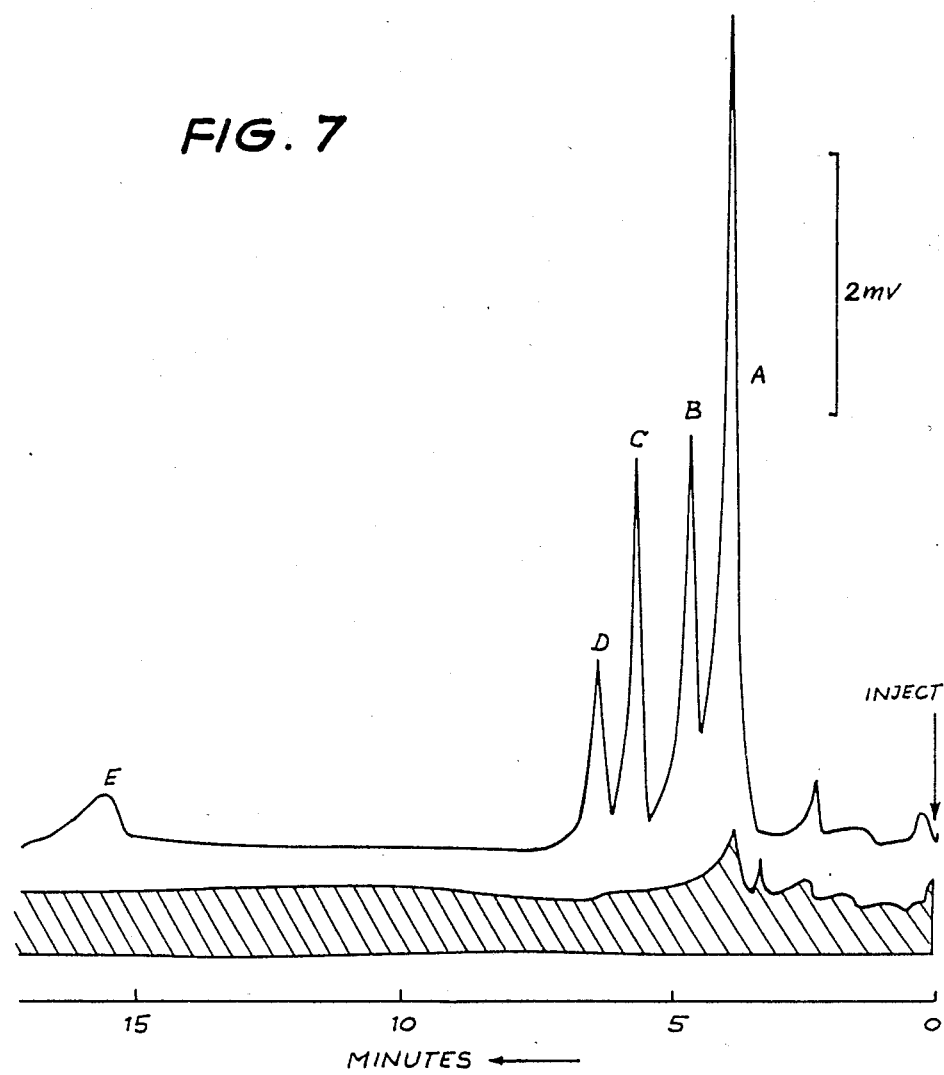
Figure 8:
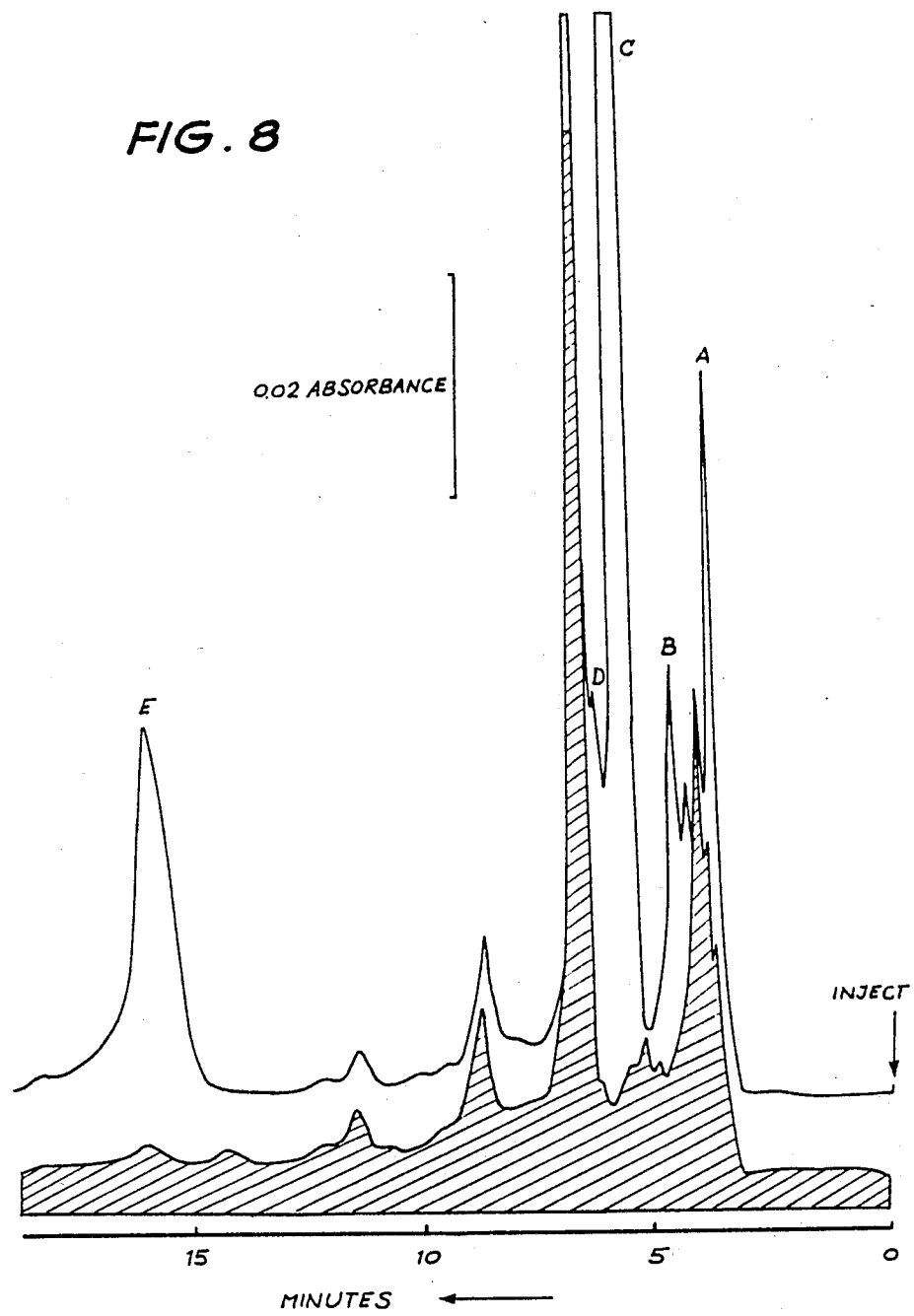

The suitability of the CTE for analysis of urine and a pharmaceutical prepartion was investigated. The freshly reconstituted urine sample was not pretreated in any way except for filtration through a Millipore filter prior to injection. The chromatograms obtained for the urine sample using both detectors are shown in FIGS. 7 and 8. These Figures also show the chromatograms obtained from urine spiked with five amino acids.

In FIGS. 7 and 8 the dark trace relates to an undiluted urine sample and a spiked urine sample (upper trace) containing the following amounts of amino acids added per ul of urine: (A) glycine (75.µg); (B) valine (5.3 µg); (C) methionine (7.6 µg); (D) isoleucine (4.1 µg); (E) phenylalamine (0.7 µg). Conditions: 1 µlinjection with a flow rate of 1 ml/min. FIG. 7 concerns the use of the detector of this embodiment and FIG. 8 the use of a UV absorbance detector (at 200 nm).

The chromatograms obtained using the UV detector are characterised by a profusion of unidentified peaks and this background renders recovery calculations of the added amino acids difficult. In contrast, the CTE chromatogram of the blank urine sample is very "clean" and the peaks produced by the added amino acids in the spiked sample are easily identified. From these chromatograms the recovery percentages for glycine, valine, isoleucine, methionine and phenylalamine were 96%, 106%, 107%, 105% and 100% respectively. The amounts of amino acids added to the spiked sample are shown in the Figure. FIG. 7 illustrated a marked advantage of the CTE, that is, its selectivity which eliminates the need for major pretreatment of the sample.

Figure 9:
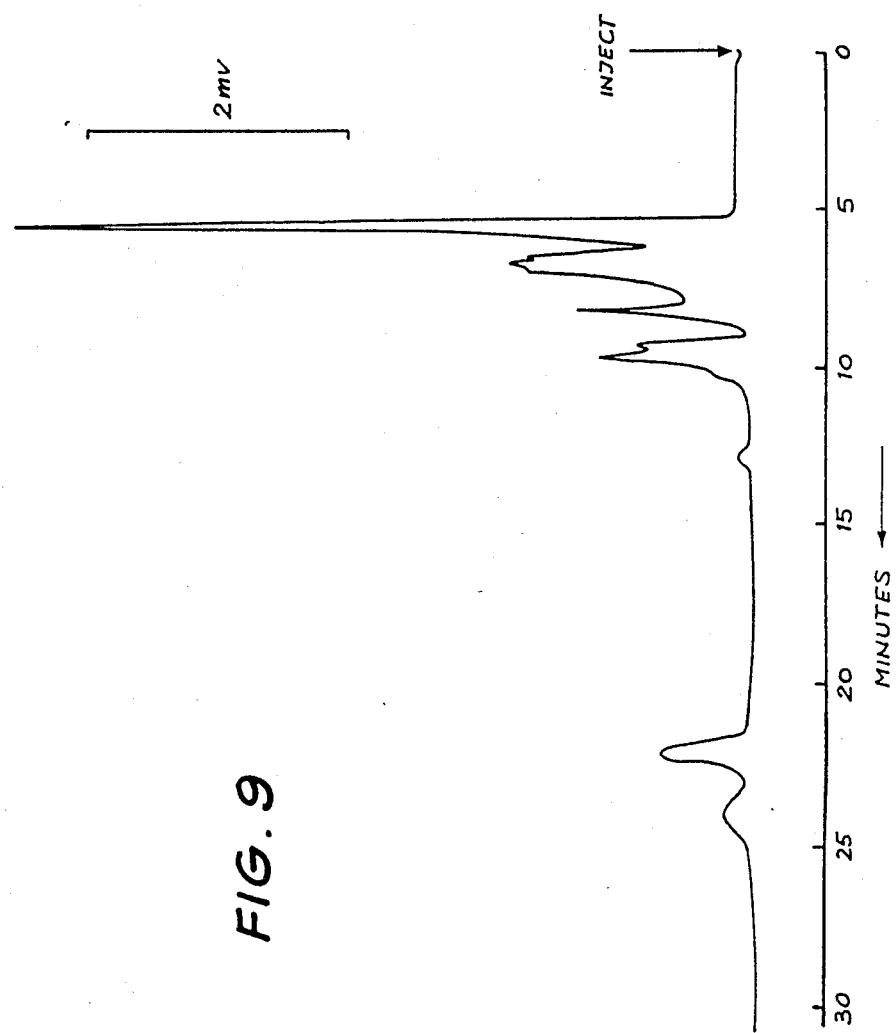

An intravenous solution containing 15 amino acids and excipients such as sodium metabisulphite, sodium acetate and sodium chloride was analysed using the CTE detector. No pretreatment of the sample was involved except dilution and filtration. The chromatogram obtained is shown in FIG. 9. No attempt was made to identify or quantify each amino acid and the separation conditions were not optimised since the purpose was merely to demonstrate the utility of the CTE for pharmaceutical analysis. However, peaks due to 11 of the 15 components can be discerned and it is likely that the remaining amino acids are eluted together with the resolved components.

This example was demonstrated that the CTE can be used as a selective detector in HPLC. In using such an electrode, problems associated with post column derivatisation procedures or absorbance detection of solutes having poor UV absorption are minimised. The performance of the CTE, as indicated by its response time and sensitivity, is comparable to that of the UV absorbance detector. Major advantages of the CTE of this embodiment are: firstly, the selectivity of the CTE is greatly superior to UV detection, and secondly the CTE can be manufactured at very low cost.

In this example, amino acids have been used as solutes to demonstrate the application of the CTE to HPLC. Other copper binding compounds may also be detectable. Narang and Gupta Ind. J. Chem. 13 (1975) 705 have shown that sulpha drugs of sulphanilamide, sulphaguanidine, sulphathiazole, sulphamerazine, sulphadiazine and sulphapyridine readily formed complexes with copper and Evans et al "High Pressure Liquid Chromatography in Clinical Chemistry", Academic Press, London, 1976, P.71-77, in their discussion of the analysis of porphyrins in biological materials by HPLC have reported that capro and meso-porphyrin esters readily complexed copper. We have found that a variety of solutes give response with the CTE.

Referring to FIG. 10, there is shown a detector 1 which is formed from perspex and comprises a 0.8 mm copper wire electrode 6 and a silver-silver chloride reference electrode 4 placed in agar-agar gel containing 0.1M potassium chloride 2. All channels 3 constituting the flow through cell in the detector 1 are of 1.5 mm diameter. Tubings for solution flow and wire electrodes are mounted in the detector 1 by means of Omnifit fittings 5.

The manifold system of FIG. 11 is used for flow-injection measurements of metal ions and comprises a multichannel peristaltic pump 7 having one outlet 8 pumping water through a rotary injection valve 9 for injecting samples into the carrier stream. Another pump outlet 10 feeds EDTA in a phosphate buffer solution.

A metallic copper electrode which has just been described in relation to FIGS. 1 to 9 as a potentiometric indicator electrode for the determination of aminoacids, may be employed to detect the presence of other copper binding ligands. In the present embodiment potentiometric sensors responsive to the concentration of free ligand can be used, both in static and flow conditions, for indirect determination of cations forming stable complexes with a chosen ligand. One possibility of performing such determinations in flow-injection systems is the gradient titration method, where the time interval between the appearance of excess of the responsive ion in the stream and its disappearance is proportional to the concentration of reacting species. One determination takes usually from a few seconds to a few hundred seconds. However, an alternative approach is used in this example for indirect determinations, performed by partial subtraction of ligand present in a carrier stream after injection of a sample solution containing complex forming cations.

In tne embodiment of FIGS. 10 and 11 measurements of potential were carried out using a pH-meter (not shown), interfaced to a strip chart recorder (not shown). Flow-injection measurements of metal ions were carried out using buffers of phosphate (0.25M $KH_2PO_4$+0.15M NaOH) or maleate (0.05M maleic acid +0.095M NaOH) of pH 6.8 containin EDTA, and 0.1M sodium chloride. All solutions being deaerated before measurements by use of a water vacuum pump.

Electrodue response to EDTA

The main property of the metallic copper electrode required was to function as an indicator electrode sensitive to ligands binding copper ions. This requires the existence of a redox couple, $Cu^0/Cu^{2+}$, at the metal-electrolyte interface. In neutral phosphate buffer, the potential of this couple is stabilized by the weak complexation of Cu(II) ions by phosphate. Increased concentration of a stronger complexing agent results in a decrease of potential of the copper electrode. Both steady-state and flow-injection measurements indicate the sensitivity of the copper metallic electrode to EDTA in phosphate buffer with slope very close to Nernstian for divalent ions. It was also observed that, in fast flow-injection measurements, better dynamic characteristics were obtained while chloride ions were present in the carrier solution without changing the Nernstian slope. Therefore, in all subsequent determinations the carrier stream besides buffer components (and EDTA in metal ion determinations) contained 0.1M sodium chloride. Detailed discussions of the effect of chloride measurements of copper binding ligands with a metallic copper electrode will be given elsewhere.

Indirect measurement of metal ions

In this analysis flow injection determination of metal ions is based on partial consumption of excess of EDTA present in the carrier stream to form stable complexes. It follows that there are two basic assumptions required: first, that the indicator electrode responds to ligand L present in the carrier stream with a constant slope S in the concentration range used; and, second, that the product of the reaction of ligand L with metal ion M (charges are omitted for simplicity; is negligibly dissociated. The potential of the indicator electrode in the presence of a ligand of concentration $c_L$ in the carrier stream can be expressed by the following equation:

$$E_1 = E^* + S \log c_L \quad (1)$$

where E* is a constant related to the standard potential value. When the injected sample contains concentration $C_M$ of the reacting cation and dilution in the flow system is given by the dispersion D according to the treatment used by Ruzicka and Hansen in Flow-Injection Analysis, published by J. Wiley and Sons, New York 1981 wherein partial consumption of ligand by the metal ions will produce an electrode potential given by:

$$E_2 = E^* + S \log \left( c_L - \frac{C_M}{D} \right) \quad (2)$$

The potential difference $E_2 - E_1 = H$ is equal to the peak height H observed as a result of injection of sample containing the cation complexed by ligand L. Subtraction of both equations leads to the relationship between the observed peak height and the concentration of metal ions in the injected sample, given by:

$$1 - 10^{H/S} = \frac{1}{c_L \cdot D} C_M \quad (3)$$

which is a linear relationship between the term $(1-10^{H/S})$ and $C_M$ with slope $(C_L \cdot D)^{-1}$. Hence, the sensitivity of such a determination decreases with increase of ligand concentration (FIG. 3) and increase of dispersion in the flow system. Simple rearrangement of Eq. 3 indicates also that at the point of the calibration plot where $C_M = C_L$ the reciprocal of the term $(1-10^{H/S})$ gives the value of dispersion in the manifold used. The low limit of ligand concentration which can be employed depends on the working range for a given ligand where response slope is constant for any indicator electrode. The peak height for different ions with the same complex stoichiometry does not depend on the stability of the formed complex providing the dissociation of the complex is negligible. If conditions similar to those used in treatment of complexometric titrations are assumed, then metal ions forming complexes of conditional stability constants $K^1 > 10^7$ should have similar peak heights for equal cation concentrations. These assumptions neglect kinetic effects which especially in fast flow-injection measurements may affect the observed response.

Experimental data shown in Table 1 confirm these assumptions when compared with calculated conditional stability constants. Included in Table 1, however, is an example of low peak heights observed for nickel (II) which is known to form a very inert EDTA complex. This inertness of nickel (II) complex formation was observed as a much higher "apparent dispersion" in the case of Ni (II) response.

The above concept of measurement can be applied for cation concentration ranges where $C_M < C_L \cdot D$. Exceeding this latter condition means introducing into the carrier stream a concentration of metal ion larger than the ligand concentration. In the case of copper (II) ions using the metallic copper electrode, extremely high potential peaks were observed. A similar situation for other metal ions is a source of curvature in the relationship given in Eq. (3) and observed on calibration plots.

In conclusion, the method of the present invention via this embodiment shows the feasibility of indirect flow-injection measurements with various other electrodes employing other ligands, giving better sensitivity and (by proper choice of ligands) better selectivity. For example, polyamines may be employed as complexing agents for some transition metal ions which can be discriminated from alkaline earth metal ions.

TABLE 1

Relationship between observed peak heights and conditional stability constants for metal ion-EDTA complexes in 0.05 M maleate buffer

| Metal ion | log $K^1$ | H* mV |
|---|---|---|
| $Ba^{2+}$ | 3.1 | 2.8 |
| $Mg^{2+}$ | 4.9 | 6.4 |
| $Ca^{2+}$ | 5.9 | 14.8 |
| $Mn^{2+}$ | 9.8 | 17.6 |
| $Zn^{2+}$ | 12.1 | 16.8 |
| $Pb^{2+}$ | 12.2 | 16.8 |
| $Cu^{2+}$ | 12.5 | 18.0 |
| $Co^{2+}$** | 12.6 | 17.6 |
| $Ni^{2+}$ | 14.2 | 12.8 |

*at pH 6.8 with peak height values obtained for injection 75 μl $10^{-4}$ M samples of given ions using $10^{-4}$ M EDTA in maleate buffer as carrier.
**Side reaction for maleate not taken into account because of unknown stability constants. All stability constant values taken from J. Inczedy, Analytical Application of Complex Equilibria, Ellis Horwood, Chichester 1976.

We claim:

1. A method of detecting amino acids and other organic copper-complexing agents in a fluid, said method comprising the steps of:

providing a potentiometric electrode detector comprising copper metal electrode located within a flow through cell, said flow through cell having a volume in the range of 0.2 pl to 2 μl and being flow-coupleable to said fluid, said detector including a tubular inlet or material inert to the fluid to be analyzed, a reference electrode located within the cell downstream of said inlet, said copper metal electrode providing a voltage response to the amino acid or other organic copper-complexing agent to be detected;

passing said fluid to be analyzed through said detector; and measuring said voltage response to thereby determine said amino acid or other organic copper-complexing agent.

2. A method according to claim 1, wherein the flow-through cell is formed from perspex.

3. A method according to claim 1, wherein the copper metal electrode is in the form of a wire.

4. A method as claimed in claim 3, wherein the reference electrode is a wire formed from silver-silver chloride.

5. A method as claimed in claim 1, wherein measurements of potential are made via of pH-meter interfaced with recording means.

* * * * *

UNITED STATES PATENT AND TRADEMARK OFFICE
CERTIFICATE OF CORRECTION

PATENT NO. : 4,589,958
DATED : May 20, 1986
INVENTOR(S) : Alexander et al

It is certified that error appears in the above-identified patent and that said Letters Patent is hereby corrected as shown below:

Column 10 line 26 delete "pl"

Column 10 line 28 delete "or" and replace by --of--

Signed and Sealed this

Twenty-sixth Day of August 1986

[SEAL]

Attest:

DONALD J. QUIGG

Attesting Officer

Commissioner of Patents and Trademarks